United States Patent [19]

Hommeltoft

[11] Patent Number: 5,900,522

[45] Date of Patent: * May 4, 1999

[54] PROCESS FOR THE PREPARATION OF AN ISOBUTANE/ISOHEXANE CONTAINING PRODUCT

[75] Inventor: Sven Ivar Hommeltoft, Hillerød, Denmark

[73] Assignee: Haldor Topsoe A/S, Lyngby, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/580,060

[22] Filed: Dec. 20, 1995

[30] Foreign Application Priority Data

Dec. 21, 1994 [DK] Denmark ................. 1460/94

[51] Int. Cl.$^6$ ........................................ C07C 6/08
[52] U.S. Cl. ........................................ 585/708
[58] Field of Search ............................. 585/708

[56] References Cited

U.S. PATENT DOCUMENTS

| | | |
|---|---|---|
| 3,668,269 | 6/1972 | Chloupek . |
| 3,686,354 | 8/1972 | Hervert ................. 585/708 |
| 3,766,292 | 10/1973 | Wall et al. . |
| 4,423,264 | 12/1983 | Juguin et al. ........... 585/255 |
| 4,613,723 | 9/1986 | Olah ...................... 585/730 |
| 5,396,016 | 3/1995 | Jablonski et al. ....... 585/708 |
| 5,489,727 | 2/1996 | Randolph et al. ....... 585/702 |

*Primary Examiner*—Mark L. Bell
*Assistant Examiner*—Patricia L. Hailey
*Attorney, Agent, or Firm*—Ostrolenk, Faber, Gerb & Soffen, LLP

[57] ABSTRACT

Process for the preparation of an isobutane/isohexane containing product comprising passing an isopentane feed to a disproportion stage and disproportionating the isopentane feed in the presence of olefinic and/or higher branched paraffinic hydrocarbons by contact with an acid catalyst having an acidity of $H_o > 8$ at a temperature of between 0° C. and 150° C. and withdrawing an isobutane/isohexane containing product.

16 Claims, No Drawings

PROCESS FOR THE PREPARATION OF AN ISOBUTANE/ISOHEXANE CONTAINING PRODUCT

BACKGROUND OF THE INVENTION

1. Field of the Invention

The present invention concerns the preparation of isobutane and isohexane containing products. More particularly, the invention relates to a process for the preparation of the those products by disproportionation of an isopentane feedstock in the presence of olefinic or branched-chain paraffinic hydrocarbons and an acid catalyst.

2. Description of the Related Art

Disproportionation of saturated hydrocarbons is a well-known reaction step in the isomerization of normal hydrocarbons to isoparaffins during petroleum refining.

Isoparaffins have a higher octane number than normal paraffins, and are, therefore, preferred components in high octane gasoline products.

During disproportionation reactions, a hydrocarbon feedstock is converted to a hydrocarbon product of higher and lower molecular weight.

Disproportionation of lower paraffinic hydrocarbons to isoparaffinic hydrocarbons is mentioned in U.S. Pat. No. 3,668,269. At the disclosed process, paraffinic hydrocarbon feed is contacted with a solid acidic catalyst comprising a platinum-group metal on a crystalline alumino-silicate. The product obtained thereby contains isoparaffin-hydrocarbons with one more and one less carbon atoms per molecule than the hydrocarbon feed.

Production of isopentane by disproportionation of $C_6$ alkanes with a catalyst comprising a Group VIII metal and a Group VIB metal is, furthermore, disclosed in U.S. Pat. No. 3,766,292.

It is also known to use $AlCl_3$ on an aluminum support or alkyl fluoride and $BF_3$ as promoters in the disproportionation of saturated hydrocarbons.

The general object of this invention is to provide a product being rich in isobutane and isohexane by catalytic disproportionation of isopentane feed.

As mentioned by way of introduction, isoparaffins including isopentane are presently preferred components in high octane gasoline products. However, recent requirements to lower vapour pressure of gasoline, makes it necessary to substitute isoparaffins having a high vapour pressure with components of lower vapour pressure in gasoline.

Isopentane may be disproportionated to isohexanes with a lower vapour pressure and to isobutane, a preferred feedstock in alkylation processes for the production of high octane alkylate gasoline and MTBE; hence, it is desirable to obtain the above substitution of isopentane in gasoline.

It has now been found that disproportionation of isopentane is catalyzed by a strong acid, and the reaction is further promoted by the presence of olefins or higher paraffins, which crack to olefins by influence of a strong acid.

SUMMARY OF THE INVENTION

Accordingly, the present invention relates to process for the preparation of an isobutane/isohexane containing product, which process comprises passing an isopentane feed to a disproportion stage, and disproportionating the isopentane feed in the presence of olefinic and/or branched higher paraffinic hydrocarbons by contact with an acid catalyst having an acidity of $H_o > 8$ at a temperature of between 0° C. and 150° C. to obtain the isobutane/isohexane containing product.

DESCRIPTION OF THE INVENTION

High yield of desired isobutane and isohexanes is obtained with acids having an acidity of the sulphuric acid or higher. The acid may be a Bronsted or a Lewis acid.

Presently, preferred acids are selected from the group of fluorinated sulphonic acids, the most preferred being trifluoromethanesulphonic acid.

An attractive feature of the present invention is its utilization of higher branched-chain paraffins in the disproportionation process. These paraffins are byproducts formed during other processes such as the production of alkylate gasoline. The carbon number of the paraffins will typically be in the range of between $C_{10}$ to $C_{30}$. Upon contact with the acid used in the disproportionation step, the crack to paraffins yield olefinic hydrocarbons.

Olefinic hydrocarbons promote the isopentane disproportionation presumably by protonation of the olefins to carbenium ions and reaction of the carbenium ions with isopentane to form an iso-$C_{10}$-carbenium ion, which finally is converted to isobutane and isohexanes. The isopentane disproportionation rate is, thereby, proportional with the olefin content in the reaction stage. High concentrations of olefins, however, result in the formation of higher molecular weight paraffinic hydrocarbon byproducts.

Thus, a preferred concentration range of olefinic and/or higher branch-chain paraffinic hydrocarbons in the process is between 0.1% and 50% by volume of the isopentane feed in the disproportionation stage.

EXAMPLES

In the Examples, a 6 meter ¼" reactor tube packed with silica (Merck 100, 0.2–0.5 mm particle size) was used. The reactor tube was thermostated in a bath, and 6 ml trifluoromethanesulphonic acid were introduced into the reactor. A feed stream as specified in Table 1 below, was passed on at a flow rate of 5 ml/min. and at a temperature of between 0° C. and 40° C. through the packed reactor.

Further process parameters and results obtained thereby are summarized in Table 1.

TABLE 1

| | Isopentane Disproportionation | | | | | | | |
|---|---|---|---|---|---|---|---|---|
| Example | 1 | 2 | 3 | 4 | 5 | 6 | 7 | 8 |
| Concentrations in % (w/w) | | | | | | | | |
| Feed: | | | | | | | | |
| Isopentane | 96 | 96 | 96 | 96 | 96 | 97 | 79.5 | 78 |
| Propylene | 3.4 | 3.4 | 3.4 | 3.4 | | | | |
| 2-butene | | | | | 4.0 | | | 3.7 |
| 1-pentene | | | | | | 3.0 | | |
| C8 | | | | | | | 0.1 | 0.1 |
| C9 | | | | | | | 2.0 | 1.7 |
| C10+ | | | | | | | 18.3 | 15.9 |
| Temperature | 0 | 20 | 30 | 40 | 40 | 40 | 40 | 40 |

TABLE 1-continued

Isopentane Disproportionation

| Example | 1 | 2 | 3 | 4 | 5 | 6 | 7 | 8 |
|---|---|---|---|---|---|---|---|---|
| Product | | | | | | | | |
| C3 | 1.45 | 1.25 | 1.26 | 1.26 | 0.00 | 0.00 | 0.00 | 0.00 |
| C4 | 4.41 | 5.79 | 6.47 | 8.49 | 9.97 | 6.90 | 4.30 | 9.13 |
| C5 | 79.66 | 77.07 | 74.52 | 68.84 | 71.21 | 77.31 | 75.23 | 52.52 |
| C6 | 4.09 | 5.16 | 6.42 | 8.29 | 9.52 | 7.32 | 3.83 | 7.92 |
| C7 | 1.29 | 1.66 | 2.04 | 2.51 | 1.33 | 1.26 | 0.61 | 2.33 |
| C8 | 2.57 | 2.99 | 3.24 | 3.98 | 0.79 | 0.40 | 0.51 | 2.08 |
| C9 | 3.05 | 3.09 | 3.18 | 3.60 | 5.44 | 4.61 | 2.63 | 8.69 |
| C10+ | 3.47 | 3.00 | 2.88 | 3.02 | 1.73 | 2.21 | 12.22 | 17.33 |

What is claimed is:

1. An improved process for the preparation of a product containing an increased yield of isobutane/isohexane, said process comprising:

passing an isopentane feed to a disproportion stage, said isopentane feed containing olefinic and branched paraffinic hydrocarbons for promoting the rate of disproportionation of isopentane in said feed;

disproportionating the isopentane feed in the presence of the olefinic and branched paraffinic hydrocarbons by contact with an acid catalyst having an acidity of $H_o>8$, such that said paraffinic hydrocarbons crack to yield additional olefins upon contact with said acid catalyst during said disproportionation step, said feed being at a temperature of between 0° C. and 150° C., wherein the disproportionation occurs under conditions effective to produce a product containing isobutane and isohexane at a rate which is proportional to the amount of olefins in said isopentane feed; and withdrawing the isobutane/isohexane containing product.

2. The process of claim 1, wherein the olefinic hydrocarbons are selected from $C_3$–$C_6$ olefinic hydrocarbons.

3. The process of claim 1, wherein the branched paraffinic hydrocarbons are selected from $C_{10}$–$C_{30}$ branched paraffinic hydrocarbons.

4. The process of claim 1, wherein the olefinic and/or branched paraffinic hydrocarbons constitute between 0.1 and 50% by volume of the isopentane feed in the disproportionation stage.

5. The process of claim 1, wherein the acid catalyst comprises a fluorinated sulphonic acid.

6. The process of claim 5, wherein the fluorinated sulphonic acid is trifluoromethanesulphonic acid.

7. An improved process for the preparation of a product containing an increased yield of isobutane/isohexane, said process comprising:

passing an isopentane feed to a disproportion stage, said isopentane feed containing olefinic hydrocarbons for promoting the rate of disproportionation of isopentane in said feed;

disproportionating the isopentane feed in the presence of the olefinic hydrocarbons by contact with an acid catalyst having an acidity of $H_o>8$, said feed being at a temperature of between 0° C. and 150° C., wherein the disproportionation occurs under conditions effective to produce a product containing isobutane and isohexane at a rate which is proportional to the amount of olefins in said isopentane feed; and withdrawing the isobutane/isohexane containing product.

8. The process of claim 7, wherein the olefinic hydrocarbons are selected from $C_3$ through $C_6$ olefinic hydrocarbons.

9. The process of claim 7, wherein the olefinic hydrocarbons constitute between 0.01 and 50% by volume of the isopentane feed in the disproportionation stage.

10. The process of claim 7, wherein the acid catalyst comprises a fluorinated sulphonic acid.

11. The process of claim 10, wherein the fluorinated sulphonic acid is trifluoromethanesulphonic acid.

12. An improved process for the preparation of a product containing an increased yield of isobutane/isohexane, said process comprising:

passing an isopentane feed to a disproportion stage, said isopentane feed containing branched paraffinic hydrocarbons for promoting the rate of disproportionation of isopentane in said feed;

disproportionating the isopentane feed in the presence of the branched paraffinic hydrocarbons by contact with an acid catalyst having an acidity of $H_o>8$, such that said paraffinic hydrocarbons crack to yield olefins upon contact with said acid catalyst during said disproportionation step, said feed being at a temperature of between 0° C. and 150° C., wherein the disproportionation occurs under conditions effective to produce a product containing isobutane and isohexane at a rate which is proportional to the amount of olefins in said isopentane feed, said olefins being present as a result of cracking of said paraffinic hydrocarbons; and withdrawing the isobutane/isohexane containing product.

13. The process of claim 12, wherein the branched paraffinic hydrocarbons are selected from $C_{10}$ through $C_{30}$ branched paraffinic hydrocarbons.

14. The process of claim 12, wherein the branched paraffinic hydrocarbons constitute between 0.01 and 50% by volume of the isopentane feed in the disproportionation stage.

15. The process of claim 12, wherein the acid catalyst comprises a fluorinated sulphonic acid.

16. The process of claim 15, wherein the fluorinated sulphonic acid is trifluoromethanesulphonic acid.

* * * * *